United States Patent [19]
Hörauf

[11] 3,955,583
[45] May 11, 1976

[54] METHOD OF AND APPARATUS FOR DENTAL ANESTHESIA

[76] Inventor: Roderich Hörauf, 8073 Kosching, Germany

[22] Filed: Aug. 5, 1974

[21] Appl. No.: 495,069

[30] Foreign Application Priority Data
Aug. 4, 1973   Germany............................ 2339648

[52] U.S. Cl............................................. 128/420 R
[51] Int. Cl.²........................................... A61N 1/34
[58] Field of Search............... 128/420, 419 R, 421, 128/422, 423, 409, 1 C

[56] References Cited
UNITED STATES PATENTS

| | | | |
|---|---|---|---|
| 2,866,461 | 12/1958 | Suzuki............................ | 128/419 R |
| 3,215,139 | 11/1965 | Dietz.............................. | 128/419 R |
| 3,563,247 | 2/1971 | Bowers........................... | 128/422 |
| 3,727,616 | 4/1973 | Lenzkes.......................... | 128/422 |

FOREIGN PATENTS OR APPLICATIONS 707,011   3/1965   Canada.................. 128/419 R OTHER PUBLICATIONS
Smith et al., "Electronarcosis by . . . Direct & Alternating Current," Am. J. of Med. Electronics, Jan.—Mar. 65, pp. 38–41., (Copy).

*Primary Examiner*—Ronald L. Frinks
*Assistant Examiner*—Lee S. Cohen
*Attorney, Agent, or Firm*—Karl F. Ross; Herbert Dubno

[57] ABSTRACT

A region to be anesthetized is connected between a pair of electrical leads. A train of like primary direct-current pulses of a polarity tending to counter nerve-generated pain signals is applied to the region by the conductors. Between these primary pulses there is applied to the region to be anesthetized direct-current secondary voltage pulses of a polarity opposite that of the primary pulses and of duration and current strength equal to only a fraction of the duration and current strength of the primary pulses. The primary and secondary pulses are both of constant current and the primary pulses have a current strength and duration equal to between 3 and 20 times the current strength and duration of the secondary pulses. A timer or clock operates a relay which serves to reverse the polarity of the voltage applied to the region to be anesthetized and to alternately connect it to either of a pair of current regulators in turn connected to a battery power supply. Circuitry is provided for monitoring direction and strength of current flow through the tooth.

10 Claims, 3 Drawing Figures

METHOD OF AND APPARATUS FOR DENTAL ANESTHESIA

FIELD OF THE INVENTION

The present invention relates to a method of and apparatus for dental anesthesia. More particularly this invention concerns such a dental anesthetic system which uses the passage of an electric current through the region to be anesthetized.

BACKGROUND OF THE INVENTION

It is known that when a nerve or the like is damaged it generates a pain signal. This current can be countered with an electrical current that is passed through the tooth.

Such a method has been shown to be effective for short periods of time, however after a period of such anesthesia, usually in the neighborhood of one minute, the pain-reducing effect of such a direct current being passed through the tooth decreases. To counteract this, it is known to alternate the current in one direction with a current of similar duration and amplitude in the opposite direction. The dentist or dental technician periodically throws a switch which reverses the polarity of the two probes in the patient's mouth and effects this alternation.

It has also been discovered that this latter system is relatively ineffective after long periods of time. It appears that the direction of current flow after predetermined periods of time becomes ineffective to eliminate nerve-generated pain signals. In addition such a system is relatively clumsy to operate, especially by a person who is often busy with more difficult tasks such as the filling of teeth or the like.

OBJECTS OF THE INVENTION

It is therefore an object of the present invention to provide an improved method of and apparatus for dental anesthesia.

Another object of this invention is the provision of a dental anesthesia method which it is simple to operate and which can provide anesthesia over long periods of time according to the above-given general principles.

SUMMARY OF THE INVENTION

These objects are attained according to the present invention in a system wherein a train of like equispaced direct-current voltage pulses of a polarity tending to counter nerve-generated pain signals is applied to the region to be anesthetized. In each of the intervals between these primary pulses there is applied to the region a direct-current secondary voltage pulse having a polarity opposite to that of the primary pulses and duration and current strength equal only to a fraction of the duration and current strength of the primary pulses. Thus according to the present invention the decreasing effectiveness of the primary pulses is eliminated by effectively jolting the tooth with a short pulse of opposite polarity so that when the primary pulse is renewed it is as effective as if it had not followed pulse of like polarity.

In accordance with the present invention the duration and current strength of the primary pulses is equal to between three and 20 times the duration of the current strength of the secondary pulses. This ratio has proven to be extremely effective in providing anesthesia of the region over a relatively long period of time.

In accordance with this invention the primary pulses last between 25 and 35 seconds, preferably 30 seconds, and the secondary pulses between 1.5 and 2.5 seconds, preferably two seconds. The current strength of the primary pulses is between 15 and 100 microamperes.

The apparatus for dental anesthesia according to the present invention comprises a voltage source connected to two current regulators so as to form a pair of constant current sources respectively generating primary and secondary outputs, the former being between three and 20 times the strength of the latter. Switch means is provided having one side connectable to the region to be anesthetized and another side connectable to the primary and secondary sources so as to apply the voltage from the primary source to the region in one direction and from the secondary source to the region in the opposite direction. A clock connected to the switch means serves to connect the region to the primary current source for a predetermined time period equal to a multiple of the time period it is connected to the secondary current source.

Such an apparatus is relatively uncomplicated. The clock means includes a transistor switch connected to a relay forming part of the switch means. The current sources themselves each include a regulating transistor in series with the switch means, an operating transistor having an output connected to the regulating transistor, and a reference-voltage source such as a zener diode connected to the regulating transistor and across the switch means.

According to further features of this invention there is provided means for indicating strength of current flow across the region to be anesthetized and means for indicating the direction of flow across this region. An ammeter and load resistor connected in series with the region being anesthetized allow the user to monitor and carefully control the amount of current flowing therethrough.

In addition according to this invention there is provided a switch which connects various different voltage outputs from the voltage source to the current sources and a sensor connected to the one side of the switch means for detecting current flow through the region and correspondingly the selector switch so as to obtain a most uniform current flow through the region by controlling the voltage input to the current regulators.

The system according to the present invention has proven effective for anesthetizing a region such as a tooth almost indefinitely. The user need not constantly readjust and operate the apparatus as it functions independently of him once it is set in operation. The circuitry is simple and virtually foolproof so that a long service life of the unit is obtained.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
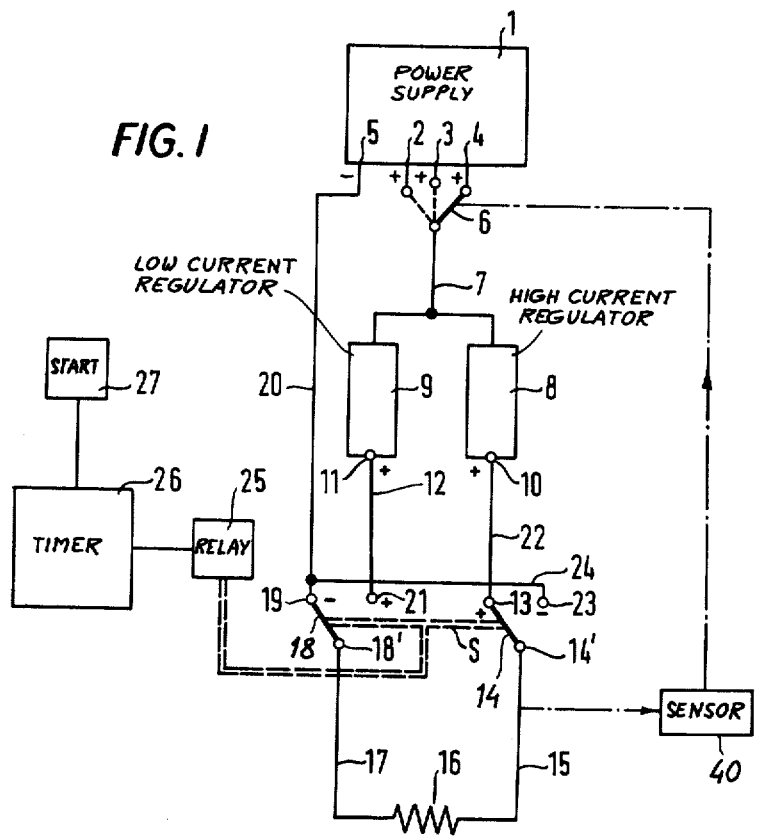
FIG. 1 is a block diagram illustrating the system according to this invention.

As shown in FIG. 1 a power supply 1 has three positive-voltage outputs 2, 3, and 4 which yield voltages of 15 volts, 18 volts, and 21 volts, respectively. In addition the power supply 1 has a negative terminal 5.

A three-position switch 6 can connect a conductor 7 to any of the three outputs, 2 - 4 and is in turn connected to high and low current regulators 8 and 9 having respective outputs 10 and 11. Conductors 22 and 12 from the outputs 10 and 11 are connected to terminals 13 and 21 of a double-pole double throw switch S having a pair of poles 18 and 14 connected to respective terminals 18' and 14' and each connectable to terminals 19 and 21, or 13 and 23, respectively. Terminals 19 and 23 are interconnected by a conductor 24 to a conductor 20 itself connected to the negative terminal 5 of the power supply 1. The switch S forms part of a relay 25 operated by a clock timer 26 itself set in operation by a starter 27.

The terminals 14' and 18' of the switch S are connected via respective leads 15 and 17 to a tooth shown schematically at 16. A sensor 40 is connected to the lead 15 to sense current flow therein and itself operates the switch 6.

Figure 1A:
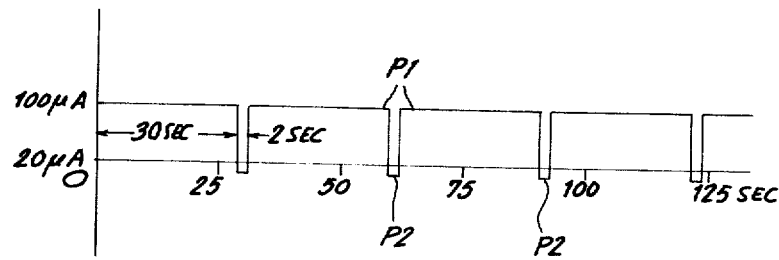
FIG. 1a is a pulse diagram illustrating operation of the system of FIG. 1.

The current regulator 8 produces a relatively high current and the current regulator 9 a relatively low current. The timer 26 operates the relay 25 so that the switch S connects the tooth 16 for a relatively long period of time between terminals 13 and 19 and for a relatively short period of time between the terminals 23 and 21, thereby also reversing the direction of current flow through the tooth 16. FIG. 1a shows how relatively large pulses P1 separated by relatively small pulses P2 are induced in the tooth 16. Pulses P1 have a current strength equal to 100 microamperes and the pulses P2 a current strength equal to 20 microamperes with opposite polarity. The pulses P1 have a duration of 30 seconds and the pulses P2 of 2 seconds.

This regulator functions as follows:

When the current drawn from output 10 increases, the voltage drop across the resistors R2 and R1 will similarly increase. This changed voltage will be sensed across resistor R3 and compared with a reference voltage which is the avalanche voltage of the Zener diode Z. The changed difference between the reference voltage and the input voltage from R3 causes a collector current to flow in the regulating transistor T2 which simultaneously is the base current from the series transistor T1. Thus the emitter/collector resistance of T1 is controlled by the transistor T2 so as to maintain the current flow at output 10 constant by increasing the resistance of transistor T1 flow as the current increases and decreasing it as the current output increases. Changes in current consumption from output 10 are caused by displacement of the electrodes connected to the tooth 16 or the lie, it being essential that the current flow of the tooth 16 remain substantially uniform. The position of switch 6 determines whether the currents at outputs 10 and 11 will be 50 and 15 microamperes, 100 and 20 microamperes, or 150 and 30 microamperes, respectively.

The clock 26 is formed of a pair of NPN transistors T3 and T4, the latter having its base connected directly to the emitter of the former. The emitter of T4 is connected to the negative ground 20 and a relay 25 operating the switch S and a resistor R9 are connected between the collector of transistor T4 and the positive line 7. Thus conduction of the transistor T4 will actuate the relay 25 and move the switch from the illustrated position.

The clock 26 is enabled by a relay 34 forming part of the starter circuit 27 and having a contact 28 which is closed so as to feed voltage to a conductor 29, a variable resistor R7, a fixed resistor R8 and a diode 31 to the base of transistor T3. A condenser 30 is connected between the base of transistor T3 and ground and has a charging time equal to 30 seconds.

In addition a variable resistor R10 and a switch 32 forming part of the relay 25 are connected between the base of transistor T3 and ground.

Thus when the switch 28 is closed the capacitor 30 will charge slowly. The time constant resistors R7 and R8 and capacitor 30 is such that after 30 seconds there will be sufficient voltage at the base of transistor T3 to cause this transistor T3 to conduct, thereby simultaneously causing the emitter follower transistor T4 also to conduct and close the relay.

Closure of the relay will reverse the current flow through the tooth 16 and connect this tooth 16 to the low-current regulator 9.

The resistor R10 and condenser 30 constitute a tuned circuit also which has a time constant of 2 seconds before the voltage applied to the base of transistor T3 drops enough to cause this transistor to become non-conductive. Transistor T4 thereby also becomes non-conductive and the relay 25 opens. The cycle is then completed with 30 seconds of connection to the high-current regulator 9 and 2 seconds to the low-current regulator 8. In all cases the current flows back into the ground 20 through a stack 33 of diodes. The low-current regulator 8 has a structure similar to that of the high-current regulator 9.

During operation of the device the dental technician can monitor the current flow through an ammeter 35 and even control this current within a limited range by means of an adjustable resistor 38 connected in the lead 15. A neon bulb 36 bridges the leads 15 and 17 and allows the operator to ascertain in which direction the current is flowing. In addition a push button switch 37 and a load resistor 41 are connected across the leads 15 and 17 so as to allow the operator to ascertain if the device is functioning properly even absent connection of the leads 15 and 17 of the tooth.

Figure 2:
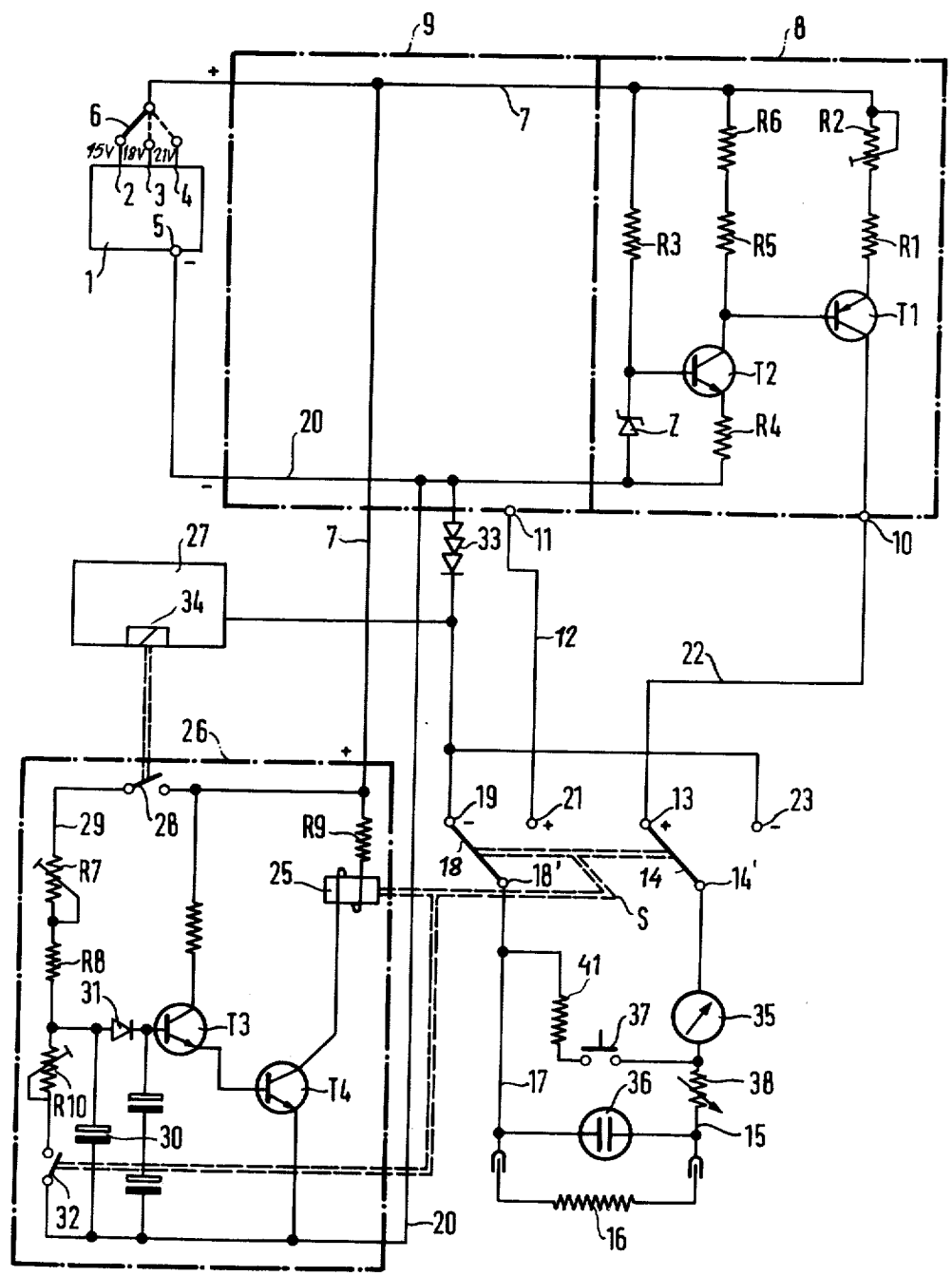
FIG. 2 is a schematic view of the system in accordance with the present invention.

The starter circuit 27 which is only shown as a block in FIG. 2 can comprise a two-stage transistor amplifier whose input is connected through the diode stack 33 to the negative line 20. This starter 27 is provided with a push button that sets the apparatus in operation.

I claim:

1. A method of dental anesthesia comprising the steps of:
 applying to the region to be anesthetized a primary train of like equispaced direct-current primary voltage pulses of a polarity tending to counter nerve-generated pain signals; and
 applying to said region in each of the intervals between said primary pulses a direct-current secondary voltage pulse of a polarity opposite to that of said primary pulses and a duration and current strength equal to a fraction of the duration and current strength of said primary pulses, said primary pulses having a duration and current strength equal to between three and 20 times the duration and current strength of said secondary pulses.

2. The method defined in claim 1 wherein the current strength of said primary pulses is between 15 and 100 microamperes.

3. A method of dental anesthesia comprising the steps of:
   applying to the region to be anesthetized a primary train of like equispaced direct-current primary voltage pulses of a polarity tending to counter nerve-generated pain signals; and
   applying to said region in each of the intervals between said primary pulses a direct-current secondary voltage pulse of a polarity opposite to that of said primary pulses and a duration and current strength equal to a fraction of the duration and current strength of said primary pulses, the duration of the primary pulses being between 25 and 35 seconds and the duration of said secondary pulses being between 1.5 and 2.5 seconds.

4. The method defined in claim 3, further comprising the step of maintaining said current strengths substantially uniform.

5. An apparatus for dental anesthesia comprising:
   a primary constant current source having a primary output with a primary current strength;
   a secondary constant current source having a secondary output with a secondary current strength equal to a fraction of said primary current strength;
   switch means having one side connectable to a region to be anesthetized and another side alternately connectable to said primary and secondary outputs for alternately applying to said region a primary voltage pulse of a polarity tending to counter nerve-generated pain signals from said primary current source and a secondary voltage pulse of opposite polarity from said secondary current source;
   clock means connected to said switch means for alternately connecting said another side thereof for a predetermined primary time period to said primary current source and for a predetermined secondary time period equal to a fraction of said primary time period to said secondary current source; and
   a voltage source connected in common to both of said current sources.

6. An apparatus for dental anesthesia comprising:
   a primary constant current source having a primary output with a primary current strength;
   a secondary constant current source having a secondary output with a secondary current strength equal to a fraction of said primary current strength;
   switch means having one side connectable to a region to be anesthetized and another side alternately connectable to said primary and secondary outputs for alternately applying to said region a primary voltage pulse of a polarity tending to counter nerve-generated pain signals from said primary current source and a secondary voltage pulse of opposite polarity from said secondary current source; and
   clock means connected to said switch means for alternately connecting said another side thereof for a predetermined primary time period to said primary current source and for a predetermined secondary time period equal to a fraction of said primary time period to said secondary current source, said clock means including a transistor switch and said switch means including a relay connected to said transistor switch.

7. An apparatus for dental anesthesia comprising:
   a primary constant current source having a primary output with a primary current strength;
   a secondary constant current source having a secondary output with a secondary current strength equal to a fraction of said primary current strength;
   switch means having one side connectable to a region to be anesthetized and another side alternately connectable to said primary and secondary outputs for alternately applying to said region a primary voltage pulse of a polarity tending to counter nerve-generated pain signals from said primary current source and a secondary voltage pulse of opposite polarity from said secondary current source; and
   clock means connected to said switch means for alternately connecting said another side thereof for a predetermined primary time period to said primary current source and for a predetermined secondary time period equal to a fraction of said primary time period to said secondary current source, said current sources each including a regulating transistor connected in series with said switch means, an operating transistor connected to said regulating transistor, and a reference-voltage source connected to said regulating transistor and across said switch means.

8. An apparatus for dental anesthesia comprising:
   a primary constant current source having a primary output with a primary current strength;
   a secondary constant current source having a secondary output with a secondary current strength equal to a fraction of said primary current strength;
   switch means having one side connectable to a region to be anesthetized and another side alternately connectable to said primary and secondary outputs for alternately applying to said region a primary voltage pulse of a polarity tending to counter nerve-generated pain signals from said primary current source and a secondary voltage pulse of opposite polarity from said secondary current source;
   clock means connected to said switch means for alternately connecting said another side thereof for a predetermined primary time period to said primary current source and for a predetermined secondary time period equal to a fraction of said primary time period to said secondary current source; and
   flow means for indicating current flow across said region and direction means for indicating direction of current flow across said region.

9. The apparatus defined in claim 8, wherein said flow means comprises an ammeter connected to said one side of said switch means and connectable in series with said region, and a variable resistor is connected to said one side of said switch means in series with said ammeter.

10. An apparatus for dental anesthesia comprising:
   a primary constant current source having a primary output with a primary current strength;
   a secondary constant current source having a secondary output with a secondary current strength equal to a fraction of said primary current strength;
   switch means having one side connectable to a region to be anesthetized and another side alternately connectable to said primary and secondary outputs for alternately applying to said region a primary voltage pulse of a polarity tending to counter nerve-generated pain signals from said primary current source and a secondary voltage pulse of opposite polarity from said secondary current source;

clock means connected to said switch means for alternately connecting said another side thereof for a predetermined primary time period to said primary current source and for a predetermined secondary time period equal to a fraction of said primary time period to said secondary current source; and a voltage source having a plurality of different voltage outputs, selector means for alternately connecting each voltage output to said current sources, and sensor means connected to said one side of said switch means for detecting current flow through said region and correspondingly operating said selector means for uniform current flow.

* * * * *